United States Patent [19]

Warden et al.

[11] 4,138,816
[45] * Feb. 13, 1979

[54] COMBINED AMALGAM CARRIER AND DENTAL HANDPIECE

[75] Inventors: Fuller Warden; Eugene W. Lewis, both of Tulsa, Okla.

[73] Assignee: Grace Development Company, Tulsa, Okla.

[*] Notice: The portion of the term of this patent subsequent to Feb. 13, 1990, has been disclaimed.

[21] Appl. No.: 668,196

[22] Filed: Mar. 18, 1976

Related U.S. Application Data

[63] Continuation of Ser. No. 508,256, Sep. 23, 1974, Pat. No. 3,965,578.

[51] Int. Cl.² .............................................. A61C 5/04
[52] U.S. Cl. .............................................. 32/60; 366/196
[58] Field of Search ............................. 32/60, 40 A, 51; 366/602, 190, 194, 195, 196

[56] References Cited

U.S. PATENT DOCUMENTS

| | | | |
|---|---|---|---|
| 3,417,971 | 12/1968 | Blank et al. | 366/196 |
| 3,552,023 | 1/1971 | Osbeck | 32/60 |
| 3,715,806 | 2/1973 | Warden | 32/60 |

Primary Examiner—Robert Peshock
Attorney, Agent, or Firm—Head, Johnson & Chafin

[57] ABSTRACT

A dental handpiece comprising a power source, plugger means, and a disposable cartridge assembly removably engagable with the power source, said plugger means being carried by the power source and selectively movable with respect to the cartridge for passing therethrough in a reciprocal movement, said cartridge including a housing preloaded with selected quantities of mercury and silver, or the like, in separate sealed compartments, and means extending through the housing and engagable with the power source for longitudinal and rotatable movement with respect to the housing, said longitudinal movement causing a combining of the initially separated mercury and silver components, said rotatable movement causing both mixing of the components to produce amalgam for denture fillings and discharging of said amalgam from the housing for engagement thereof by the plugger means, and said plugger means being selectively reciprocal through the cartridge for implanting multiple charges of the amalgam in a tooth cavity, or the like, and packing the charges in the cavity.

8 Claims, 8 Drawing Figures

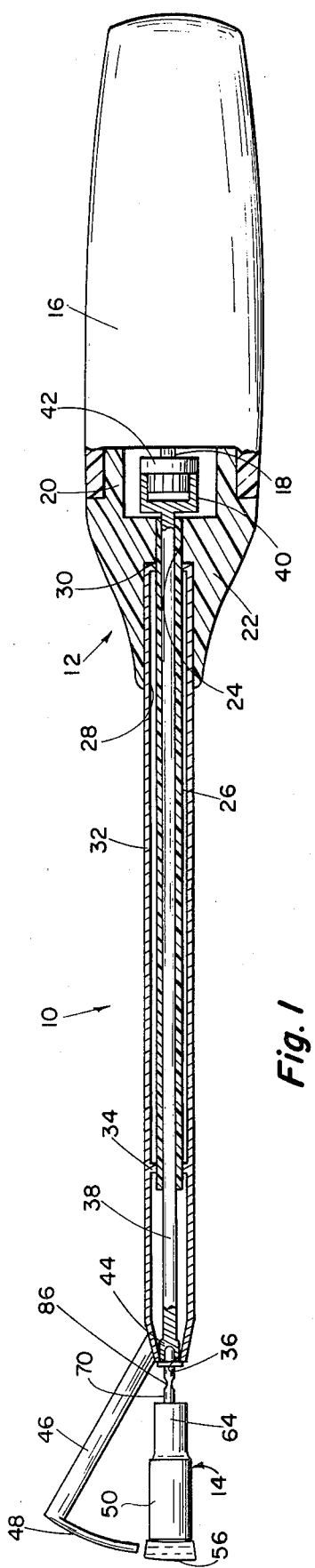
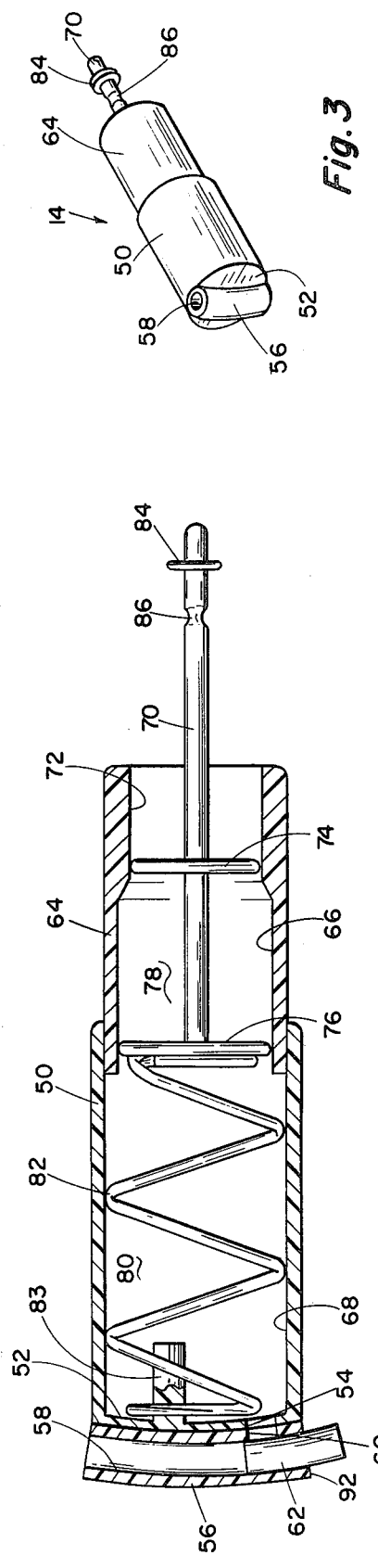
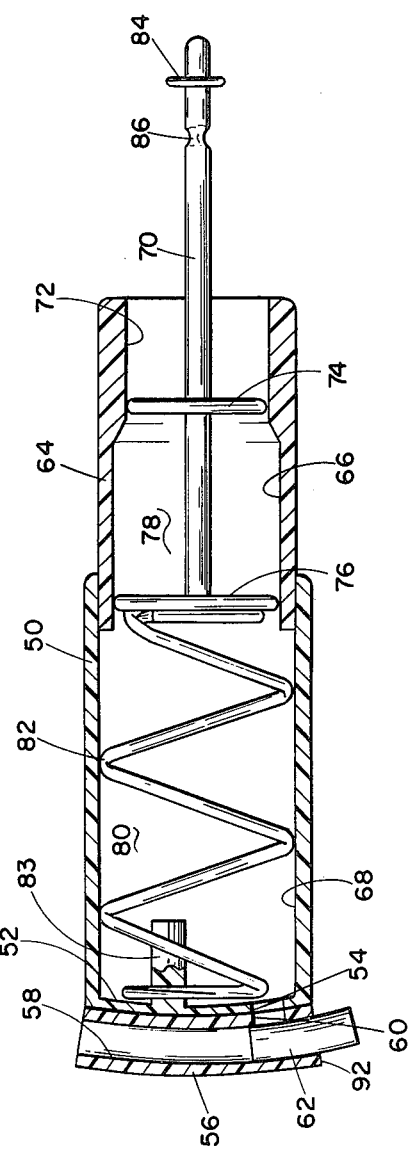

COMBINED AMALGAM CARRIER AND DENTAL HANDPIECE

This application is a continuation of our co-pending application, Ser. No. 508,256, filed Sept. 23, 1974 and now U.S. Pat. No. 3,965,578 issued June 29, 1976, and entitled, "Combined Amalgam Carrier and Dental Handpiece".

BACKGROUND OF THE INVENTION

1. Field of the Invention

This invention relates to improvements in dental equipment, and more particularly, but not by way of limitation, to a combined amalgam carrier and plugger tool for dental use.

2. Description of the Prior Art

The usual method in widespread use today for filling a tooth cavity with amalgam, or the like, comprises placing a preselected quantity of silver and mercury in a suitable vessel or container for mixing thereof to produce the amalgam. A carrier tool is then filled with a charge of the amalgam and hand carried to the cavity for depositing the amalgam therein. Subsequent to placing a charge of amalgam in the tooth cavity, a second hand tool commonly known as a plugger, is utilized for compacting or packing the amalgam into the cavity. It is usually necessary to place a plurality of amalgam charges in the cavity, with a plugging operation subsequent to the placing of each amalgam charge in the cavity. In the event the cavity is relatively large, it is frequently necessary to refill the carrier tool with an additional supply of amalgam. Thus, the filling of a tooth cavity becomes tedious and time consuming in that the mixing of the components of the amalgam and cleaning of the mixing equipment is time consuming, and the use of two separate instruments for placing the amalgam in the cavity and for tamping or packing the amalgam into the cavity is cumbersome and inefficient.

SUMMARY OF THE INVENTION

The present invention contemplates an amalgam carrier in combination with a powered plugger tool particularly designed and constructed for overcoming the above disadvantages. The novel combination comprises a powered handpiece for removably receiving a disposable cartridge thereon. The cartridge is preloaded with the components of the amalgam in separate compartments for precluding any premature combining of the ingredients. When the cartridge is secured to the power portion of the tool, the ingredients are combined, and mixing means within the cartridge is actuated by the power tool for thoroughly mixing with the components of the amalgam. Plugger means is carried by the power tool and passes into and through a transverse passageway provided in the cartridge for engaging a quantity or charge of the amalgam and placing the amalgam in a tooth cavity. The plugger may then be utilized for compacting or tamping the amalgam within the cavity, and for picking up additional charges into the cavity until the cavity is efficiently filled. The entire tooth filling operation is quickly and easily effected or accomplished with the use of a single tool, and subsequent to the filling of the cavity, the cartridge may be discarded.

BRIEF DESCRIPTION OF THE DRAWINGS

FIG. 1 is a side elevational view partly in section of a dental hand tool embodying the invention.

FIG. 2 is an enlarged sectional elevational view of a cartridge such as used in the invention.

FIG. 3 is a perspective view of a cartridge such as used in the invention.

DESCRIPTION OF THE PREFERRED EMBODIMENTS

Figure 4:
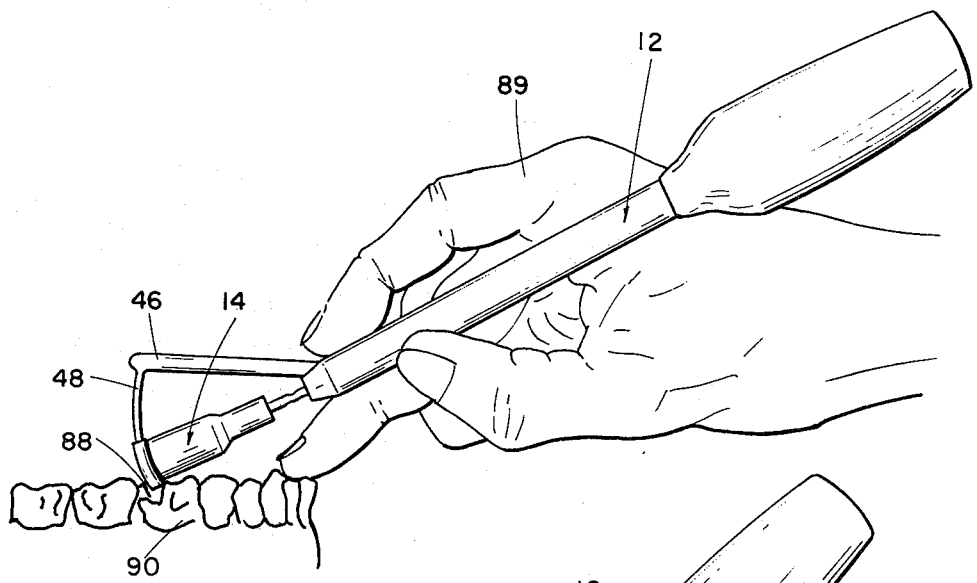
FIG. 4 is a side elevational view of a dental hand tool embodying the invention in one position of use in the filling of a tooth cavity.

Referring to the drawings in detail, reference character 10 generally indicates a dental hand tool comprising a power tool portion 12 and a cartridge 14 removably engageable therewith. Whereas the power tool portion 12 may be of any suitable type, such as that used with an electric toothbrush, or the usual dentist's handpiece, as shown herein, the portion 12 comprises a handle member 16 encasing a suitable power supply (not shown) which may be either an electric motor, or a battery powered motor, or the like, having a rotatable drive shaft 18. The handle 16 is preferably removably secured to a sleeve member 20 of a stub member 22 for facilitating access to the power source when necessary to repair the motor or recharge the batteries, or the like.

A central passageway 24 extends longitudinally through the stub member 22 into communication with the interior of the sleeve member 20 for receiving one end of a bushing sleeve 26 therethrough. The bore or passageway 24 is enlarged at 28 to provide an annular shoulder for receiving one end of an outer housing 32 thereagainst which is concentrically disposed around the outer periphery of the bushing 26 and preferably extends longitudinally therebeyond as shown in FIG. 1, but not limited thereto. An inwardly directed annular shoulder 34 is preferably provided on the inner periphery of the outer housing 32 in the proximity of the outer extremity of the bushing 26 for receiving the bushing 26 therethrough to support the bushing 26 concentrically within the housing 32. The outer extremity of the housing 32 is preferably inwardly tapered to provide a reduced opening 36 for a purpose as will be hereinafter set forth.

A rotatable shaft 38 extends through the bushing 26 and is provided with an enlarged head member 40 at one end thereof disposed within the sleeve 20 for operable engagement with a suitable drive gear or transmission element 42 carried by the drive shaft 18 whereby rotation of the drive shaft 18 will be transmitted to the shaft 38. The opposite end of the shaft 38 is provided with a suitable coupling member 44 which may be in the form of an enlarged socket for removably receiving the cartridge 14 therein as will be hereinafter set forth. The socket or coupling member 44 is preferably disposed within the reduced opening 36 and is rotatable simultaneously with the shaft 38. Of course, a suitable starter switch (not shown) may be provided on the outer periphery of the outer housing 32 with suitable electrical connection (not shown) extending through the annular space between the bushing 26 and housing 32 and through the stub member 22 in any suitable manner for connection with the power source in order that actuation of the power source may be controlled by the operator of the tool 10 in the usual or well-known manner. Alternately, internal switch means (not shown) may be provided which may be actuated during operation of the tool 10 as will be hereinafter set forth. In addition, an angularly and outwardly extending prod or support member 46 is secured to the housing 32 in any suitable manner, preferably in the proximity of the outer extremity thereof as shown in the drawings. A plugger member 48 is secured to the outer end of the support 46 and extends substantially radially outwardly therefrom in a manner and for a purpose as will be hereinafter set forth. As clearly seen in FIG. 1, it is preferable that the plugger member 48 be of a longitudinally arcuate configuration, but not limited thereto.

The cartridge 14 is preferably disposable, but not limited thereto, and as shown herein comprises a first sleeve or housing 50 preferably constructed from a suitable plastic material and having one end thereof closed by a wall 52 having a port 54 (FIG. 2) provided therein. A transversely extending diametrically disposed tubular member 56 having a central passageway 58 extending therethrough is secured to the exposed surface of the wall 52 or may be integral therewith, as desired, and the passageway 58 is preferably of a longitudinally arcuate configuration for receiving the plugger member 48 therethrough for a purpose and in a manner as will be hereinafter set forth. The sleeve or tube member 56 is provided with an aperture 60 in the sidewall thereof disposed in substantial alignment with the port 54, and it is preferable to provide a removable plug member 62 in one end of the passageway 58 for at least temporarily sealing the apertures 54 and 60.

The opposite end of the sleeve or housing 50 is open for receiving one end of a second housing 64 therein. The housing 64 is preferably constructed from a suitable plastic material and may be secured to the housing 50 in any suitable manner, such as by a press fit, cementing, or the like, and is provided with a central bore 66 therein open to and in substantial alignment with a central bore 68 provided in the housing 50. A rod or shaft member 70, preferably constructed from a suitable plastic material, extends longitudinally through the bore 66 and terminates substantially at the juncture between the housings 64 and 50, as shown in FIG. 2. From an inspection of FIG. 2, it will be apparent that the diameter of the bore 66 is preferably slightly less than the diameter of the bore 68, and the inner diameter of the sleeve 64 is reduced at 72 to provide a bore portion having a diameter slightly less than the diameter of the chamber 66 for a purpose as will be hereinafter set forth.

A pair of spaced flanges or discs 74 and 76 are secured to the rod 70 for selective engagement with the inner periphery of the housing 64. The disc 74 is preferably of a smaller diameter than the diameter of the disc 76, whereby the disc 74 may be initially disposed in engagement with the periphery of the bore 72, and the disc 76 may be disposed in engagement with the bore 66, thus separating the ieterior of the sleeves 64 and 80 ito separate and sealed compartments 78 and 80, for a purpose as will be hereinafter set forth.

As shown in FIG. 2, the rod 70 terminates substantially at the juncture between the sleeves 50 and 64 and is provided with a suitable spiral mixer-wiper member 82 which extends longitudinally from the shaft 70 and and is provided with a suitable spiral mixer-wiper member 82 which extends longitudinally from the shaft 70 and through the sleeve 50. The spiral element 82 is preferably constructed from a suitable plastic material and is secured to the shaft 70 in any suitable manner for rotation simultaneously therewith and wipes the inner periphery of the sleeve 50 during rotation thereof for a purpose as will be hereinafter set forth. In addition, a stub shaft member 83 is suitable secured to the inwardly directed surface of the wall 52 offset from the center thereof and extends longitudinally into the chamber 80 for receiving the free end of the mixer member 82 therearound for facilitating the mixing operation.

The outer extremity of the shaft 70 extends axially outwardly from the wall 65, and a circumferential flange 84 is spaced slightly from the outer end of the rod 70 for engagement with the end of the housing 32 when the rod 70 is inserted within the socket or coupling member 44. A reduced diameter portion is provided around the outer periphery of the rod 70 interposed between the flange 84 and the wall 65 to provide flexibility for the rod 70 exteriorly for the housing 64 for a purpose as will be hereinafter set forth. Of course, it is to be understood that whereas the shaft 70 as shown herein is of a substantially cross-sectional configuration, the shaft may be of substantially any desired cross-sectional configuration, and the reduced portion may be of any configuration as required to provide a flexing or pivot point in the shaft 70.

The cartridge 14 is preloaded with selected quantities of silver and mercury, or any other suitable ingredients desired for use in producing amalgam or other material for filling tooth cavities, or the like. For example, the housing 64 may be placed in a mercury bath, and the rod 70 and discs 74 and 76 inserted therein, whereby mercury is sealed within the chamber 78. The desired quantity of silver may then be placed or deposited within the housing 50 in any well-known manner, and the filled housing 64 may be press fitted in the open end of the housing 50 for sealing the silver in the chamber 80. Of course, plug 62 seals the ports 64 and 60, and in this manner the silver and mercury ingredients or components are stored within the cartridge 14 and are efficiently maintained in sealed chambers for precluding any accidental premature combining of the two components. The filled or preloaded cartridge 14 may be stored until it is desired to mix the components therein for use in the filling of a tooth cavity, or the like.

When it is desired to use the apparatus 10 for filling a cavity 88 in a tooth 90 (FIGS. 4 and 5), the handpiece 12 may be held in the hand 89 of the dentist or operator of the equipment in the usual manner. As hereinbefore set forth, the powered handpiece 12 may be the dentist's usual powered handpiece, and there is no intention of limiting the invention to an independent handpiece as shown herein. The shaft 70 may be inserted within the coupling or socket 44 and removably retained therein in any well-known manner. The shaft 70 is inserted within the socket 44 until the flange 84 engages the outer end of the housing 32 as shown in FIG. 1. The shaft 70 is thus held against longitudinal movement, and the housings 50 and 64 may be manually moved slightly further in a direction toward the housing 32 whereby the disc 76 will be displaced from its sealed position against the bore 66. The disc 76 will be moved into the chamber 80, and the mercury contained within the chamber 78 will be admitted into the chamber 80 therearound. The disc 74 will slide along the bore 72, but will preferably maintain a sealing engagement thereagainst for precluding loss of the mercury from the chamber 78 therearound. In addition, the disc 74 will facilitate the discharge of the mercury from the chamber 78 and into the chamber 80.

The power source may then be activated in the usual manner for transmitting rotation to the shaft 70 whereby the mixer-wiper element 82 will be rotated within the chamber 80 for mixing the sliver and mercury together for producing the amalgam for filling the cavity 88. The mixer element 82 wipes the periphery of the chamber 80 and constantly agitates the mixture therein for assuring an efficient mixing of the silver and mercury.

Figure 5:
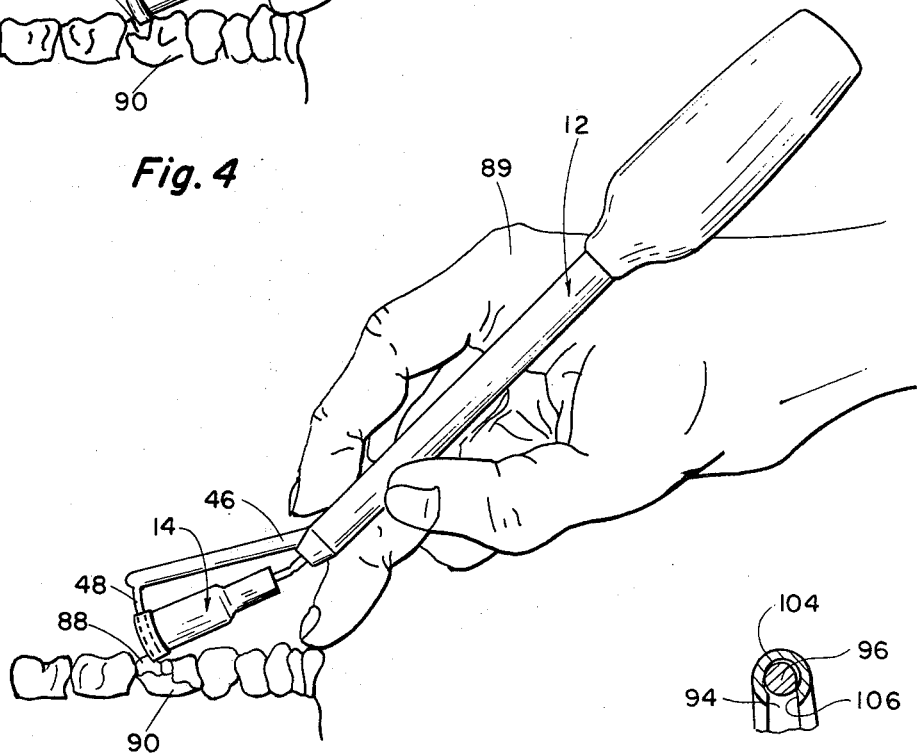
FIG. 5 is a view similar to FIG. 4 illustrating a second position of use in the filling of a tooth cavity.

The tip 92 (FIG. 2) of the tube 56 may then be manually placed against the finger of the operator, or the like, and the application of manual pressure of the tip 92 against the finger will cause the shaft 70 to flex at the point 86 whereby the longitudinal axis of the handpiece 12 will become angularly disposed with respect to the longitudinal axis of the cartridge 14 as particularly shown in FIG. 5. This action causes the plugger member 48 to move into and through the passageway 58. The outer end of the plugger member 48 will engage the plug 62, and continued application of manual pressure will cause the plugger 48 to move the plug 62 out of the passageway 58 for opening the ports 54 and 60. The pressure may then be released for removing the plugger 48 from the passageway 58.

Figure 8:
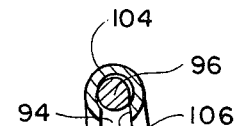
FIG. 8 is a sectional view taken on line 8—8 of FIG. 6.
Figure 6:
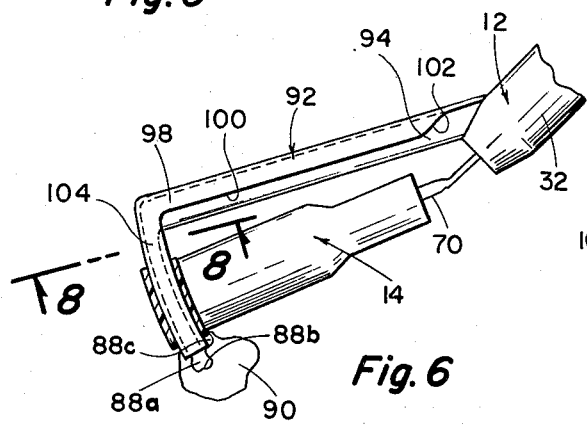
FIG. 6 is an enlarged side elevational view of a modified plugger assembly embodying the invention and depicts one position thereof in use.
Figure 7:
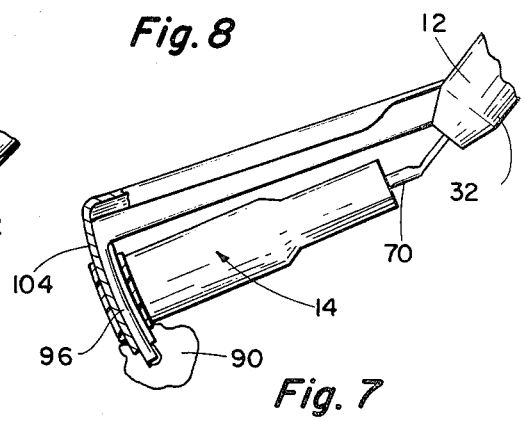
FIG. 7 is a view similar to FIG. 6 depicting another position of use for the modified plugger assembly.

The tip 92 may be placed against the edge of the tooth 90 with the passageway 58 being disposed in substantial alignment with the cavity as shown in FIG. 4. Manual pressure may then be applied against the tooth 90 whereby the plugger 48 will again enter the passageway 58. Substantially simultaneously with the application of the additional pressure against the tooth, the power source may again be activated for rotating the shaft 70, whereby the mixer member 82 will urge the amalgam within the chamber 80 in a direction toward the wall 52, and a portion of the amalgam will be forced into the passageway 58. Of course, the timing of the ejection of the amalgam into the passageway 58 is preferably such that a charge of amalgam is deposited within the passageway 58 just before the plugger 48 passes therethrough. Thus, the outer end of the plugger 48 will engage the amalgam within the passageway 58 and carry the amalgam into the cavity 88. The plugger 48 may be reciprocated slightly within the passageway by a slight rocking action of the handpiece 12 without a complete withdrawal thereof from the passageway, whereby the outer end of the plugger 48 will pack or tamp the amalgam within the cavity 88. When it is necessary to inject more amalgam into the cavity 88, the plugger 48 may be withdrawn from the passageway 58 a sufficient distance for clearing the ports 54 and 60 in order that an additional charge of amalgam may be ejected into the passageway 58, and the procedure may be repeated until the cavity 88 has been efficiently filled and packed with amalgam. Of course, the cartridge 14 may be discarded subsequent to the tooth filling operation and replaced with a new cartridge prior to initiating another tooth filling operation Referring now to FIGS. 6, 7 and 8, a modified plugger assembly 92 is shown which is of a multiple-plugger construction comprising a first support arm 94 generally similar to the arm 46 and having one end thereof suitably secured to the outer end of the housing 32 in the proximity of the tapered end portion thereof. The free end of the support arm 94 is provided with a substantially radially extending relatively small plugger member 96 of a longitudinally arcuated configuration and either integral therewith or secured thereto in any suitable manner. A flexible or spring-like substantially tubular arm member 98 having a longitudinally extending opening or slit 100 is loosely disposed over the outer periphery of the support arm 94 oppositely disposed with respect to the cartridge 14, and is secured to the housing 32 in the proximity of the support arm 94 as shown in FIGS. 6 and 7. A pivot-notch 102 is provided in the spring-arm 100 preferably in substantial alignment with the flex point or pivot point 86 of the shaft 70. The outer end of the spring-arm 98 is provided with a substantially radially extending tubular plugger member 104 having a longitudinally arcuate configuration complementary to the configuration of the relatively small plugger member 96. In addition, the plugger 104 is provided with a longitudinally extending slit or opening 106 (FIG. 8) for transversely receiving the plugger 96 therethrough upon assembly of the plugger 96 with the plugger 104. The internal diameter of the plugger 104 is preferably substantially the same size as the outer diameter of the plugger 96 whereby the pluggers 96 and 104 may be used complementary to one another to provide a relatively large plugger member, but is of a size to provide sufficient clearance between the pluggers 96 and 104 whereby the plugger 96 may be extended beyond the plugger 104 for independent use of the relatively small plugger 96.

For example, most tooth cavities, such as the cavity 88a shown in FIGS. 6 and 7, comprise cavity portions 88b of relatively small size and in open communication with cavity portions 88c of relatively large size. In the filling of these cavities, it is usually necessary to use a relatively small plugger for packing the amalgam into the cavity 88b, and a relatively large plugger for packing the amalgam in the cavity 88c. In any event, it is usually necessary to utilize a relatively large plugger member for completing the packing of a tooth filling, even in the event the entire cavity area is sufficiently small for use of only a small plugger.

The use of the plugger assembly 92 is substantially identical to the use of the plugger 46–48 as hereinbefore set forth. However, the advantage of the multiple-plugger assembly 92 is that multi-sized pluggers may be provided in a single dental hand tool. When the relatively small plugger 96 is to be used, the plugger 104 will be engaged by the sides of the larger cavity portion 88c as shown in FIG. 7, and continued pressure of the cartridge 14 against the tooth 70 will cause the plugger 96 to move longitudinally with respect to the plugger 104 for extension of the plugger 96 axially outwardly therefrom for insertion into the smaller cavity portion 88b. This assures that the amalgam will be deposited in the cavity portion 88b and efficiently packed therein. When the relatively large plugger 104 is needed, the pressure of the cartridge 14 against the tooth 90 may be lessened whereby the plugger 96 and plugger 104 function together, as shown in FIG. 6 for assuring an efficient placement and packing of the amalgam in the larger cavity portion 88c.

Whereas only two size pluggers are shown in the plugger assembly 92 as shown herein, it will be apparent that substantially any desired number of plugger members may be similarly arrange for cooperation to provide substantially any desired plugger sizes for efficiently filling a tooth cavity with amalgam, or the like.

From the foregoing, it will be apparent that the present invention provides a novel dental handpiece comprising a power portion for removably receiving a preloaded cartridge member therein, said cartridge member being provided with the proper ingredients or components for producing amalgam, or the like, for filling a tooth cavity. When the cartridge is properly assembled with the power portion, the components of the amalgam contained therein are combined and mixed for producing amalgam, and charges of the amalgam are ejected from the mixing chamber. Plugger means is carried by the power portion and is particularly constructed for reciprocal movement through the cartridge assembly for moving a charge of amalgam from the cartridge into the tooth cavity and for tamping or packing the amalgam therein. A multiple number of charges of amalgam may be deposited in the tooth cavity and individually packed therein, as required for the efficient filling of the tooth cavity. Subsequent to the filling of the cavity, the cartridge may be discarded, and a new cartridge may be utilized for performing a second or succeeding tooth filling operation. The novel dental handpiece is simple and efficient in operation and economical and durable in construction.

Whereas the present invention has been described in particular relation to the drawings attached hereto, it should be understood that other and further modifications, apart from those shown or suggested herein may be made within the spirit and scope of this invention.

What is claimed is:

1. Cartridge means comprising a housing, mixing means disposed within said housing, sealing means carried by said mixing means and selectively engagable with a portion of said housing to provide at least two sealed chambers therein for storing quantities of ingredients preloaded therein, said mixing means operable for selectively combining and mixing said ingredients to produce an amalgam, a transverse passageway provided on the housing and being in selective communication with one of said chambers for receiving portions of the mixed ingredients therefrom.

2. Cartridge means as set forth in claim 1 constructed of a plastic material.

3. Amalgam cartridge means preloaded with at least two ingredients in separate sealed compartments, transverse passageway means provided in said cartridge means and in communication with at least one of said compartments, mixing means provided in said cartridge means, said mixing means being selectively movable within said cartridge means for release of the two ingredients from the respective sealed compartments and rotatable to combine and mix the two ingredients to produce a mixture thereof and for ejecting said mixture into said passageway means, and wherein seal means is carried by said mixing means for providing said sealed compartments.

4. Amalgam cartridge means preloaded with at least two ingredients in separate sealed compartments, transverse passageway means provided in said cartridge means and in communication with at least one of said compartments, mixing means provided in said cartridge means, said mixing means being selectively movable within said cartridge means for release of the two ingredients from the respective sealed compartments and rotatable to combine and mix the two ingredients to produce a mixture thereof and for ejecting said mixture into said passageway means, and including stub shaft means extending into one of said compartments and cooperating with said mixing means for facilitating said mixing operation.

5. Disposable amalgam cartridge means comprising a housing, one end of said housing being closed by a wall having a port therein, a rotatable shaft extending into the opposite end of the housing, a pair of spaced flanges mounted on said shaft for selective engagement with spaced apart portions of the inner surfaces of the housing, spiral mixing means connected to one end of said rotatable shaft and disposed within said housing, the opposite end of said rotatable shaft extending away from said housing for connection to suitable driving means, a transverse passageway connected to the closed wall of the housing and communicating with said port on said wall, and including longitudinally extending stub shaft means provided in said housing for cooperating with said spiral mixing means.

6. Disposable cartridge means as set forth in claim 5 wherein said rotatable shaft is flexible and the transverse passageway has a longitudinally arcuate configuration.

7. Disposable amalgam cartridge means comprising a first housing, one end of said housing being closed by a wall having a port therein, the opposite end of the housing being open, a second housing having an open end disposed in contact with the open end of the first housing and secured thereto, the opposite end of said second housing having a reduced inner diameter for receiving a rotatable shaft, said rotatable shaft extending through said reduced diameter end, a pair of spaced apart flanges mounted on said shaft, one of said flanges in selective engagement with the inner periphery of said second housing and the other of said flanges in selective engagement with the reduced diameter portion of said second housing, spiral mixing means connected to one end of the rotatable shaft and disposed within the first housing, the other end of said shaft extending away from said second housing for connection to suitable drive means, a tubular transverse passageway connected to the closed wall of the first housing and communicating with the port in said wall, and including longitudinally extending stub shaft means provided in said first housing for cooperating with said spiral mixing means.

8. Disposable cartridge means as set forth in claim 7 wherein the rotatable shaft is flexible and the transverse passageway has a longitudinally arcuate configuration.

* * * * *